`US011040348B2`

(12) United States Patent
Segura

(10) Patent No.: US 11,040,348 B2
(45) Date of Patent: Jun. 22, 2021

(54) BIOLOGICAL SAMPLE ANALYSIS KIT AND SAMPLE COLLECTION UNIT WITH A CAP HAVING AN ACCESS OPENING

(71) Applicant: Siemens Healthcare Diagnostics Inc., Tarrytown, NY (US)

(72) Inventor: Nicolas Segura, Hightstown, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 295 days.

(21) Appl. No.: 16/301,625

(22) PCT Filed: May 18, 2017

(86) PCT No.: PCT/US2017/033302
§ 371 (c)(1),
(2) Date: Nov. 14, 2018

(87) PCT Pub. No.: WO2017/201268
PCT Pub. Date: Nov. 23, 2017

(65) Prior Publication Data
US 2019/0283021 A1 Sep. 19, 2019

Related U.S. Application Data

(60) Provisional application No. 62/339,491, filed on May 20, 2016.

(51) Int. Cl.
*G01N 33/543* (2006.01)
*B01L 3/00* (2006.01)
*G01N 21/78* (2006.01)

(52) U.S. Cl.
CPC .......... *B01L 3/50825* (2013.01); *G01N 21/78* (2013.01); *G01N 33/54346* (2013.01);
(Continued)

(58) Field of Classification Search
CPC ......... B01L 3/50285; B01L 2200/0689; B01L 2200/085; B01L 2300/047;
(Continued)

(56) References Cited

U.S. PATENT DOCUMENTS 4,207,988 A * 6/1980 Prouty .................. A61J 1/1406
215/232
5,921,419 A * 7/1999 Niedospial, Jr. ...... A61J 1/2096
215/247
(Continued)

FOREIGN PATENT DOCUMENTS

WO 2006007455 A1 1/2006
WO WO-2006007455 A1 * 1/2006 .......... B01L 3/50825
(Continued)

OTHER PUBLICATIONS

European Search Report and Written Opinion of European Application No. 17800159.0 dated Apr. 3, 2019.
(Continued)

*Primary Examiner* — Benjamin R Whatley
*Assistant Examiner* — John McGuirk
(74) *Attorney, Agent, or Firm* — Dunlap Codding P.C.

(57) ABSTRACT

An embodiment of the present disclosure is a sample collection unit configured to receive a test strip. The sample collection unit includes a collection tube including an open end and a cap configured to be coupled to the open end to close the collection tube. The cap includes an access opening that extends through the cap and at least one sealing member aligned with the access opening. The at least one sealing member includes a dynamic strip interface that permits insertion of the test strip through the access opening and into the collection tube.

17 Claims, 8 Drawing Sheets

(52) U.S. Cl.
CPC ............... *G01N 33/54366* (2013.01); *B01L 2200/0689* (2013.01); *B01L 2200/085* (2013.01); *B01L 2300/047* (2013.01); *B01L 2300/048* (2013.01)

(58) Field of Classification Search
CPC ............ B01L 2300/048; G01N 21/78; G01N 33/54346; G01N 33/54366
See application file for complete search history.

(56) References Cited

U.S. PATENT DOCUMENTS

| | | |
|---|---|---|
| 6,669,908 B2 | 12/2003 | Weyker et al. |
| 7,244,392 B1 * | 7/2007 | Konecke ............. A61B 10/007 422/408 |
| 8,747,333 B2 | 6/2014 | Burkholz |
| 2004/0099628 A1 * | 5/2004 | Casterlin .......... G01N 33/54366 215/247 |
| 2015/0157300 A1 | 6/2015 | Ealovega et al. |

FOREIGN PATENT DOCUMENTS

| | | | | |
|---|---|---|---|---|
| WO | WO-2007016421 A2 * | 2/2007 | ............... | G09F 3/00 |
| WO | 2014164478 A1 | 10/2014 | | |
| WO | WO-2014164478 A1 * | 10/2014 | .......... | B01L 3/50825 |

OTHER PUBLICATIONS

International Search Report and Written Opinion of International Application No. PCT/US2017/033302 dated Aug. 16, 2017.

\* cited by examiner

BIOLOGICAL SAMPLE ANALYSIS KIT AND SAMPLE COLLECTION UNIT WITH A CAP HAVING AN ACCESS OPENING

This application claims priority to U.S. Provisional Application No. 62/339,491, filed May 20, 2016, the disclosure of which is hereby incorporated by reference in its entirety.

TECHNICAL FIELD

The present disclosure relates to a biological sample analysis kit including a sample collection unit and a test strip, and in particular to a sample collection unit having a collection tube and a cap with an access opening configured to receive the test strip.

BACKGROUND

Diagnostic methods may include testing a biological sample to measure sample properties and/or to detect substances of interest that may be present in the biological sample. In the field of urinalysis, a so-called dip-and-read test strip may be used. Such a test strip usually has one or more test areas, such as reagent pads. Each test area is capable of undergoing a color change in response to contact with a liquid specimen, in this case, a urine sample. The liquid sample usually contains one or more analytes of interest. The presence and concentrations of these analytes of interest in the sample are determinable by an analysis of the color changes undergone by the reagent pads that have been submerged in the liquid sample. The analysis may be done manually or using test equipment, including, for example, a spectrophotometer.

A typical dip-and-read test is carried out by collecting the urine sample in a standardized collection tube. A cap is attached to the collection tube to enclose the urine sample in the collection tube and prevent sample escape during storage and transport to the location where the test is carried out. In order to complete the test, the cap is removed from the collection tube. The test strip is then dipped into the collection tube to submerge the reagent pads in the urine sample. Adequate test results require that the liquid sample completely wet out each reagent pad on the test strip. In some cases, the volume of the sample in the collection tube may not be sufficient to wet out each reagent pad without some manipulation of the collection tube and test strip by the lab technician. For instance, if test strip is inserted into the collection tube when the collection tube is held vertically, then only a few of the reagent pads are submerged in the sample due to the volume of the sample in the collection tube. To address this situation, the lab technician turns the collection tube with test strip on its side to ensure that each reagent pad is fully submerged and wetted out by the sample in the collection tube. This action gives rise to a potential biohazard in the event that any of the sample escapes the collection tube when the collection tube is turned on its side.

SUMMARY

An embodiment of the present disclosure is a sample collection unit configured to receive a test strip. The sample collection unit includes a collection tube including an open end and a cap configured to be coupled to the open end to close the collection tube. The cap includes an access opening that extends through the cap and at least one sealing member aligned with the access opening. The at least one sealing member includes a dynamic strip interface that permits insertion of the test strip through the access opening and into the collection tube when the cap is coupled to the open end of the collection tube.

Another embodiment of the present disclosure is a sample analysis kit. The sample analysis kit includes a test strip that includes at least one test area arranged along the test strip. The sample analysis kit also includes a sample collection unit. The sample collection unit has a collection tube that includes an open end and a cap that is configured to be coupled to the open end to close the collection tube. The cap includes an access opening that extends through the cap and at least one sealing member aligned with the access opening. The at least one sealing member includes a dynamic strip interface that permits insertion of the test strip through the access opening and into the collection tube when the cap is coupled to the open end of the collection tube.

Another embodiment of the present disclosure is a cap for coupling to an open end of a sample collection tube. The cap includes a cap body having an upper end, a lower end opposite the upper end, and an access opening that extends through the cap body. The cap body also includes at least one sealing member aligned with the access opening. The at least one sealing member includes a dynamic strip interface. The dynamic strip interface permits insertion of the test strip through the access opening.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown. In the drawings.

DETAILED DESCRIPTION OF ILLUSTRATIVE EMBODIMENTS

Figure 1:
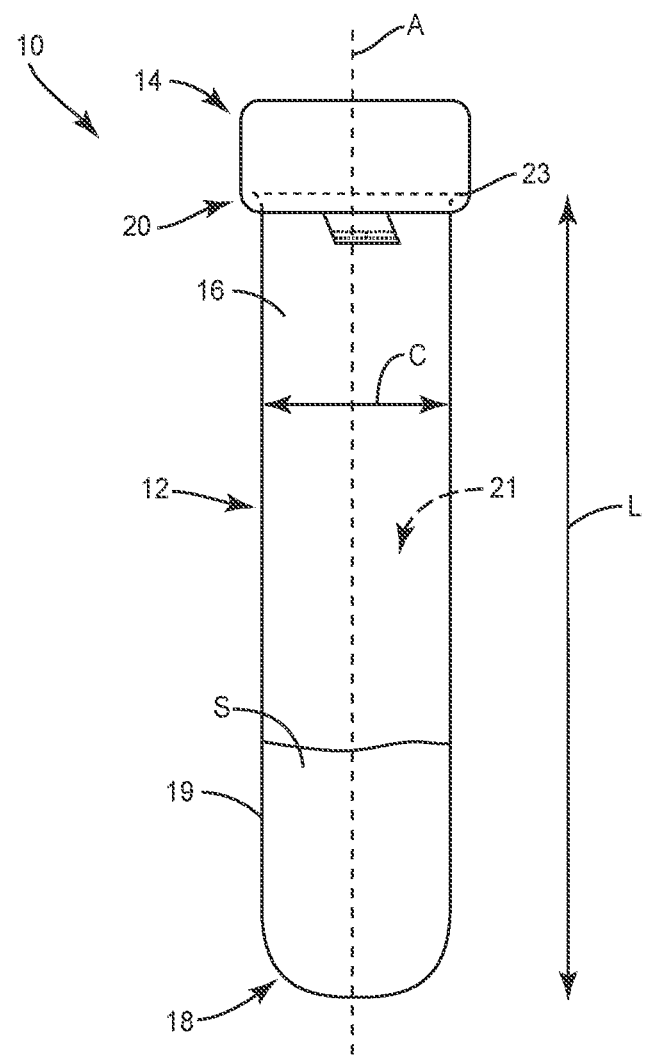
FIG. 1 is a side view of a sample collection unit including a biological sample according to an embodiment of the present disclosure.
Figure 2:
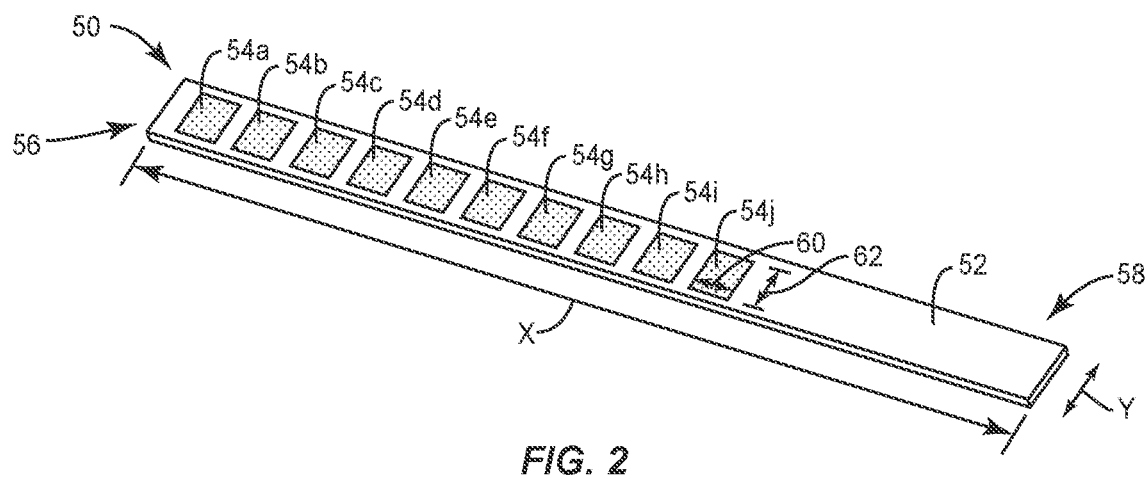
FIG. 2 is a perspective view of a test strip used to analyze a sample contained in the sample collection unit shown in FIG. 1.
Figure 3:
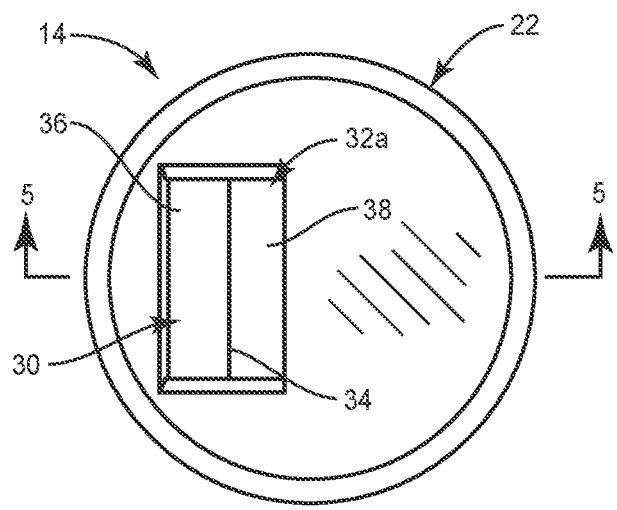
FIG. 3 is a top view of the cap illustrated in FIG. 1.

Referring to FIGS. 1-3, embodiments of the present disclosure include a biological sample analysis system that includes a sample collection unit 10, a test strip 50, and a test device (not shown) used to analyze the test strip 50. The sample collection unit 10 includes a collection tube 12 and a cap 14 adapted to close the collection tube 12. The collection unit 10 contains a biological sample S for testing. The test device (not shown) is designed to analyze the test strip 50 after it has been submerged in the biological sample S contained in the sample collection unit 10 as further explained below. The cap 14 has an access opening 30 (FIG. 3) designed to receive the test strip 50. The cap 14 is designed to inhibit the biological sample S inside the collection tube 12 from exiting the collection tube through the cap 14. For instance, when the cap 14 is coupled to the collection tube 12, the cap 14 closes the collection tube to inhibit the biological sample S from escaping the collection tube 12. The cap 14 also inhibits the biological sample S inside the collection tube 12 from exiting the collection tube 12 through the cap 14 when 1) the test strip 50 is inserted through the dynamic strip interface 34, and 2) the collection tube 12 is turned on its side so that the biological sample S contacts reagent pads 54a-54j along the test strip 50. The collection unit 10 as described herein may be used for urinalysis and the biological sample can be a urine sample. However, the collection unit 10 may be used in the analysis of liquids other than urine—such as, for instance, whole blood or water.

Referring to FIG. 2, an exemplary test strip 50 for use in analyzing a biological sample is illustrated. The test strip 50 is a planar elongate strip with a length X that extends from a forward or insertion end 56 to a rear or proximal end 58, and a width Y. The test strip 50 includes a non-reactive surface 52, which is typically white in color, and a plurality of test areas 54a-54j. Each test area 54a-54j is in the form of a reagent pad. Each reagent pad 54a-54j is provided with a different reagent which causes a color change in response to the presence of a certain type of constituent in a sample such as leukocytes (white blood cells), red blood cells, glucose, bilirubin, urobilinogen, nitrite, protein, ketone bodies, or other analytes of interest. The color developed in response to a particular analyte defines the characteristic discrete spectrum for absorption of light for that particular analyte. For example, the characteristic absorption spectrum for color-developed glucose falls within the upper end of the blue spectrum and the lower end of the green spectrum. In the illustrated embodiment, ten distinct reagent pads 54a-54j are provided on the test strip 50. Each reagent pad has a length dimension 60 that is aligned with the length X of the test strip 50 and a width dimension 62 that is aligned with the width Y of the test strip 50. An exemplary test strip can be a MULTISTIX® 10SG strip, having the length X of approximately 4.25 inches, and a width Y of approximately 0.2 inches.

Each test area 54a-54j is capable of undergoing a color change in response to contact with the biological sample S contained in the collection unit 10. The biological sample, for example a urine sample, usually contains one or more analytes of interest. The presence and concentrations of these analytes of interest in the biological sample are determinable by an analysis of the color changes undergone when the reagent pads are wetted out by the sample. Usually, this analysis involves a color comparison between the reagent pad and a color standard or scale. The comparison may be done manually by a skilled technician or by a test device.

The test device as used herein can analyze analytes of interest in the biological sample S that have been applied to the reagent pads on the test strip 50. For example, the test device may be a spectrophotometer that determines the color of the sample applied to one or more of the reagent pads 54a-54j by illuminating the reagent pad and taking a number of reflectance readings. Each reflectance reading has a magnitude relating to a different wavelength of visible light. Test devices may employ a variety of area array detection read-heads utilizing CCD (charge-coupled device), CID (charge-injection device) or PMOS detection structures for detecting color changes to the reagent pads. The color changes can be used to determine the presence of analytes of interest.

Referring to FIG. 1, the sample collection unit 10 includes a collection tube 12 and a cap 14. The cap 14 can seal a biological sample S inside in the collection tube 12 during the testing procedure to avoid potential spillage and biohazards in the lab. The collection tube 12 has an elongated body 16 that extends along a central longitudinal axis A, a bottom end 18 and an open end 20 spaced apart from the bottom end 18 along the central longitudinal axis A. The elongated body 16 includes a sidewall 19 that extends from the bottom end 18 to the open end 20. The bottom end 18 and sidewall 19 define an internal chamber 21 that contains the biological sample S when deposited therein. The collection tube includes a ridge 23 at the open end 20 that is used to facilitate attachment of the cap 14 to the collection tube 12. The collection tube 12 defines a length L that extends from the bottom end 18 to the open end 20 along the central longitudinal axis A and a cross-sectional dimension C that is perpendicular to the length L. The length L and cross-sectional dimension C of the collection tube 12 can vary as needed based on the type of test procedure contemplated. The sample collection tube 12 may have a circular cross-section about the central longitudinal axis A. However, other cross-sectional shapes could be used. A biological sample S from a patient is collected inside the collection tube 12, the cap 14 is attached to the open end 20, and the collection unit 10 is stored in standardized racks designed to receive such collection units.

Figure 4:
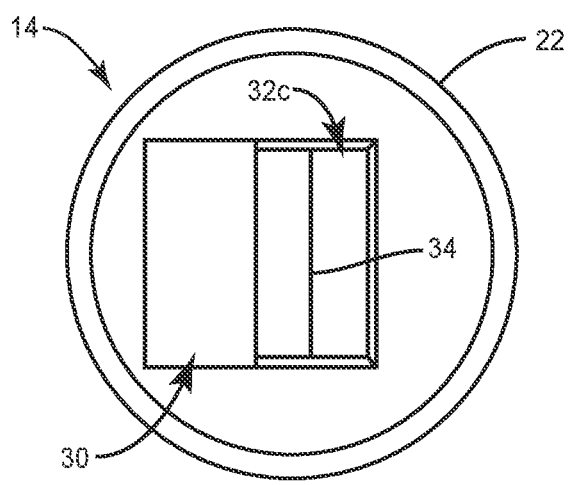
FIG. 4 is a bottom view of the cap illustrated in FIG. 1.
Figure 5:
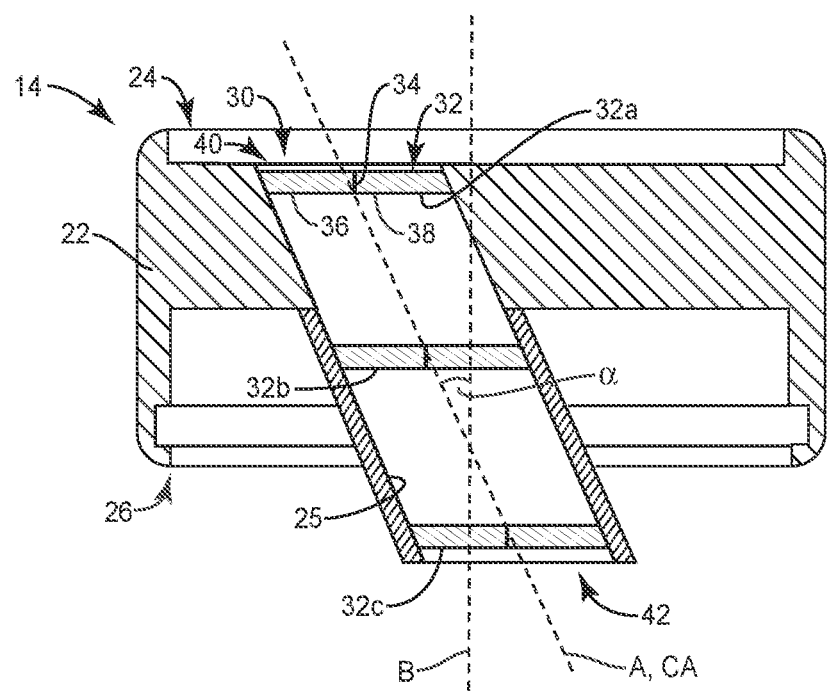
FIG. 5 is a cross-sectional view of the cap taken along line 5-5 in FIG. 3.

Referring to FIG. 3-5, the cap 14 is configured to be coupled to the open end 20 to close the collection tube 12. The cap 14 includes a cap body 22 having an upper end 24, a lower end 26 opposite the upper end 24 along a cap axis CA, and an access opening 30 that extends through the cap body 22. The cap body 22 defines an inner surface 25 that substantially defines the access opening 30. The cap body 22 also defines a groove 27 sized to receive the ridge 23 on the collection tube 12. In this regard, the cap 14 may be press-fit onto the collection tube 12. The present disclosure is not limited to a press-fit connection between the cap 14 and collection tube 12 as illustrated. Any typical mechanism for coupling the cap 14 to the collection tube 12 could be used. For example, the cap 14 can be threadably attachable to the collection tube 12. In such an example, the cap 14 and collection tube 12 includes threads that mate with each other. It should be appreciated that the cap 14 seals the collection tube 12 to prevent escape of the biological sample S from the collection tube 12. However, the word "seal" may not include a perfect seal due to typical manufacturing variances and user error in attaching the cap 14 to the collection tube 12. In this regard, it can be said that the cap 14 inhibits the biological sample S from escaping from the collection tube 12.

Continuing with reference to FIG. 3-5, the cap 14 also includes at least one sealing member 32 aligned with the access opening 30. The illustrated cap 14 includes a plurality of sealing members 32a-32c. As used herein, reference signs 32 and 32a-32c are interchangeable for purposes of describing the sealing member in the present disclosure. Each sealing member 32 defines a dynamic strip interface 34. The dynamic strip interface 34 1) permits insertion of the test strip 50 into the collection tube 12, and 2) inhibits the biological sample S inside the collection tube 12 from exiting the collection tube when the test strip 50 is inserted through the access opening 30, as further explained below Referring to FIG. 5, the plurality of sealing members 32a-32c are spaced apart with respect to each other along the access opening 30. The cap 14 includes a first sealing member 32a, a second sealing member 32b, and a third sealing member 32c, each defining a dynamic strip interface 34. The sealing members 32a-32c are spaced apart with respect to each other at a distance that is no less than the length dimension 60 (FIG. 2) of each respective reagent pad of the test strip 50. This distance permits each reagent pad to be contained between two adjacent sealing members 32 as the test strip 50 is inserted through the opening. Alternatively, each sealing member 32a-32c is spaced apart with respect to each other at a distance that varies between adjacent pairs of sealing members. For example, the distance between sealing member 32a and 32b may be less than the distance between the sealing member 32b and sealing member 32c. In such an embodiment, as the test strip 50 is inserted through the access opening 30, the sealing member 32a rides along the surface of the reagent pad while the adjacent sealing member 32b rides along the non-reactive surface 52 between two reagent pads. This allows at least one sealing member to be substantially closed against the test strip to avoid the situation where all sealing members are slightly open so that a sample could escape out of the access opening. While the cap 14 is shown with three sealing members 32, the cap 14 can include one sealing member, two sealing members, or more than three sealing members as needed.

Continuing with FIG. 5, in accordance with the illustrated embodiment, each sealing member 32 includes a first flexible tab 36 and a second flexible tab 38 opposite to the first flexible tab 36. The first flexible tab 36 and the second flexible tab 38 each extend inward into contact with each other to define the dynamic strip interface 34. The first flexible tab 36 and the second flexible tab 38 each flex so as to slide along opposed surfaces of the test strip 50 as the test strip 50 is moved through the access opening 30. For example, the first and second flexible tabs 36 and 38 are flexible enough so that the first and second tabs 36 and 38 bend and ride along reagent pads and the non-reactive surface 52 of the test strip 50 when the forward end 56 of the test strip 50 is inserted through the access opening 30. When the test strip 50 is removed from the access opening 30, the first flexible tab 36 and the second flexible tab 38 each flex back in to contact with each other to form a seal inhibiting the biological sample S contained in the collection tube 12 from exiting the collection tube 12 when the collection tube 12 is turned on its side.

Figure 6:
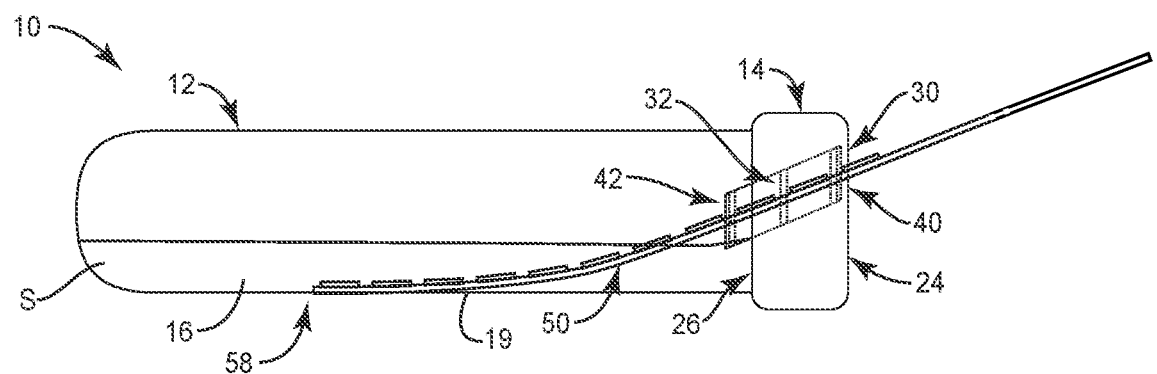
FIG. 6 is a side view of the sample collection unit with a sample contained in the collection tube and the test strip inserted through the cap in contact with the sample.
Figure 7:
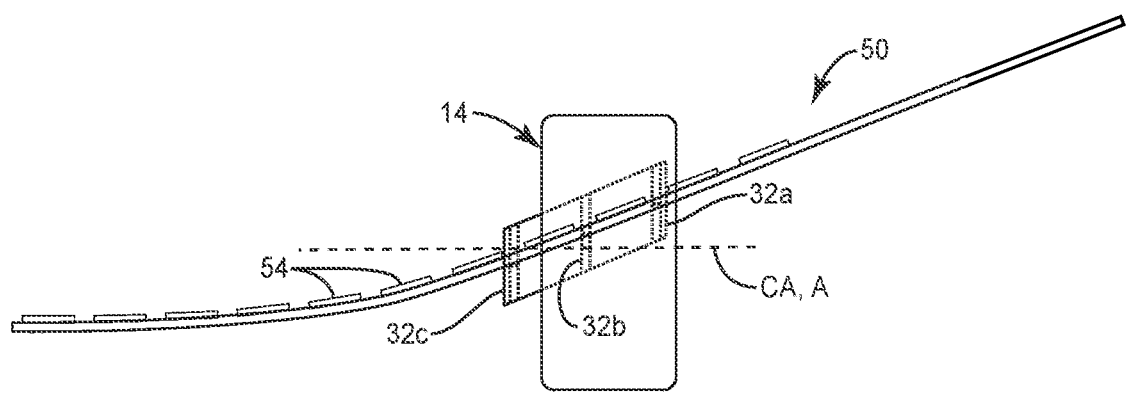
FIG. 7 is a detailed side view of the cap with the test strip inserted therein illustrated in FIG. 6.
Figure 8:
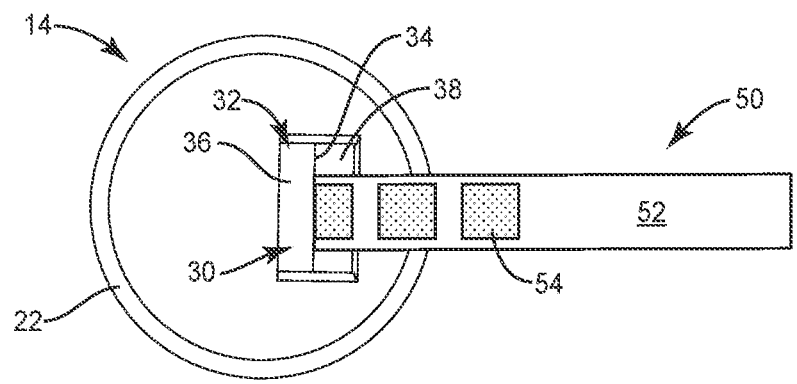
FIG. 8 is a top view of the sample collection unit with the test strip inserted through the cap as illustrated in FIG. 6.
Figure 9:
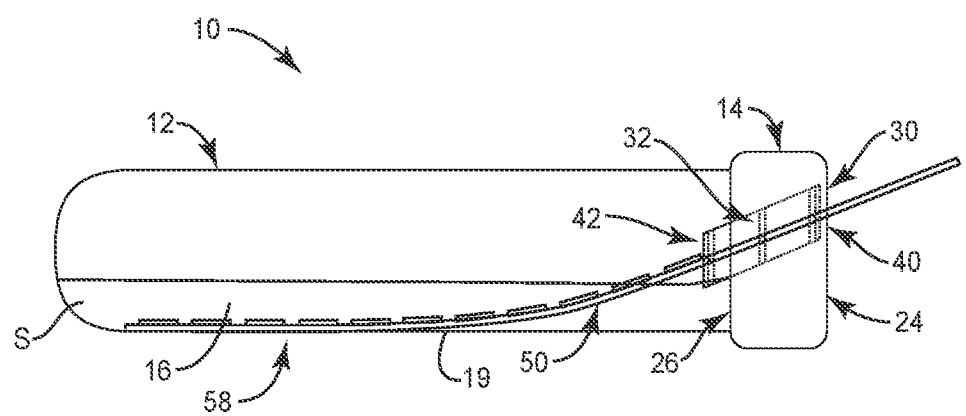
FIG. 9 is a side view of the sample collection unit with a sample contained in the collection tube and the test strip fully inserted through the cap in contact with the sample.

Continuing with FIG. 5, the access opening 30 may be arranged to inhibit the biological sample S from exiting the collection tube 12 when the collection unit 10 is turned on its side. The access opening 30 includes a first end 40 aligned with the upper end 24 of the cap body 22 and a second end 42 that opens into the collection tube 12. The second end 42 of the access opening is offset with respect to the first end 40 to an extent that prevents the biological sample S inside the collection tube 12 entering the second end 42 of the access opening from exiting the first end 40 of the access opening 30 when the collection tube 12 is turned on its side (FIGS. 6 and 9). The extent of offset between the first end 40 and the second end 42 of the access opening 30 is based in part on the orientation of access opening 30 through the cap 14. It should be appreciated that the orientation of the access opening 30 prevents the biological sample S from exiting the collection tube 12 when a typical volume of a biological sample S is contained in the collection tube 12. A typical volume of biological sample S as used herein is dependent on the size of the collection tube 12 and specific type of analysis that is being performed. A person of ordinary skill would appreciate that sample volumes can vary among different types of tests. Furthermore, the sample volume contained in the collection tube 12 can vary among different test instances.

Referring to FIGS. 5 and 6, the orientation of the access opening 30 also aids in wetting out each reagent pad 54 of the test strip 50 when it is fully inserted into the collection tube 12. For example, the offset between the first end 40 and the second end 42 aids in forcing the test strip 50 to contact and deflect against the sidewall 19 of the collection tube 12. This results in the portion of the test strip 50 that contains the reagent pads 54 to be next to and substantially parallel with the sidewall 19 of the collection tube 12 when the test strip 50 is an inserted position (see FIGS. 6 and 9). This results in more efficient wetting of each reagent pad—especially when there is low sample volume.

Continuing with FIG. 5, the access opening 30 is elongate along an access opening axis B that is angularly offset with respect to the central longitudinal axis A, as shown in FIG. 5. The access opening axis B intersects the central longitudinal axis A (or cap axis CA) and defines an acute angle α. For example, the angle α can be greater than 0 degrees and some value less than 90 degrees, such as 60 degrees. In one example, the angle α can be greater than 0 degrees and less than or equal to 60 degrees. In another example, the angle α can be greater than 0 degrees and less than or equal to 45 degrees. In another example, the angle α can be greater than 0 degrees and less than or equal to 30 degrees. Alternatively, the access opening axis B is aligned with the central longitudinal axis A, whereby the access opening 30 is substantially aligned with the central longitudinal axis A. In such an embodiment, the access opening 30 can be centered in the cap 14. However, the access opening 30 can be offset from the center of the cap 14 such that the access opening axis B is offset and parallel to the central longitudinal axis A. It should be appreciated therefore that the angle α can range from about (and including) 0 degrees to less than 90 degrees, depending on the cross-sectional dimension of the cap 14.

The cap 14 can be manufactured as a monolithic unit that defines the access opening 30. The first and second flexible tabs 36 and 38 may be coupled to or adhered to the cap body 22 in the access opening 30. Alternatively, the cap body 22 can define an inner opening that extends from the upper end 24 to the lower end 26 of the cap body 22. The inner opening is sized to receive an insert. The insert, in turn, defines the access opening 30 and the sealing members 32. It should be appreciated that the cap 14 can be manufactured using a number of different manufacturing methods.

An exemplary test procedure is describe below with reference to FIGS. 6-9. During the test procedure, the collection unit 10 inhibits a sample S contained inside the collection tube 12 from exiting the collection tube 12 or cap 14 when the test strip 50 is inserted into the collection tube through the dynamic strip interface 34 in the access opening 30. The test procedure begins when the requisite volume of a biological sample S is placed inside the collection tube 12. The cap 14 is press-fit or otherwise attached as described herein onto open end 20 of the collection tube 12. The user turns the collection unit 10 on its side so that the collection tube 12 is substantially horizontal. This results in the sample S being spread along one side of the interior of the collection tube 12. Because the access opening 30 is angled with respect to the central longitudinal axis A, it is possible to orient the collection unit 10 so that the first end 40 of the access opening 30 is elevated above the second end 42 of the access opening 30 with respect to a horizontal direction.

The user can insert a forward end 56 of the test strip 50 into the access opening 30 and into engagement with the dynamic strip interface 34 defined by the sealing member 32. As the test strip 50 is further inserted through the access opening 30, the forward end of the test strip 50 is guided into the collection tube 12 in contact with the sidewall 19 and is submerged in the sample S, as shown in FIG. 6. The orientation of the access opening 30 aids in guiding the test strip 50 into contact with the sidewall 19 until a portion of the test strip 50 with the reagent pads 54 is next to and substantially parallel to the sidewall 19 (see FIGS. 6 and 9). Further advancement of the test strip 50 through the access opening 30 guides the test strip along the sidewall 19 until substantially all of the reagent pads 54 are submerged in the biological sample S. The orientation of the access opening 30 (such as angle α) can be selected so as to maximize the extent of test strip submersion in the biological sample S when the collection unit 10 is on its side, as shown in FIG. 6.

When collection unit 10 is on its side, the first end 40 of the access opening 30 is elevated above the second end 42 of the access opening 30 such that any sample S that enters the access opening 30 through the second end 42 does not pass through the access opening 30 up the inner surface 25 and out of the first end 40. If, however, the volume of the sample S in the collection tube 12 is such that sample S could enter the access opening 30 and reach the first end 40 of the access opening 30, the sealing members 32a-32c can inhibit progression of the sample S through the access opening 30.

As the test strip 50 is removed, the sealing members 32a-32c can scrape off any of the sample S riding along the reagent pads to prevent passage of the sample through the access opening 30 and out of the collection unit 10.

Figure 10:
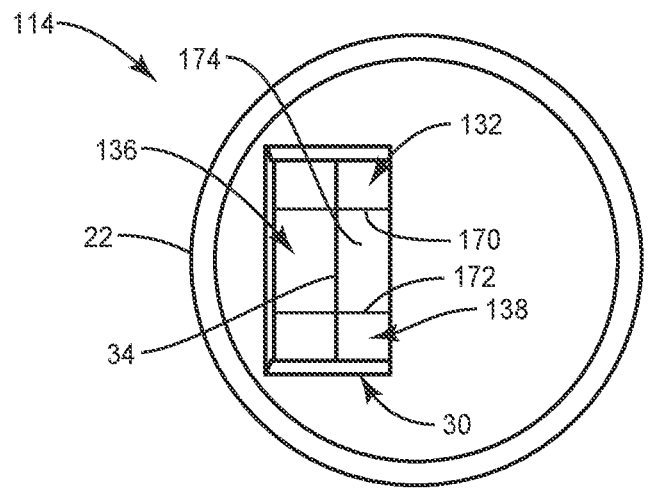
FIGS. 10-12 illustrate a cap according to another embodiment of the present disclosure.
Figure 11:
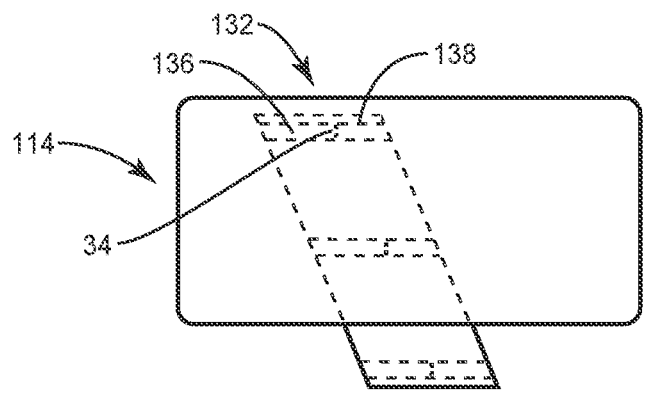
Figure 12:
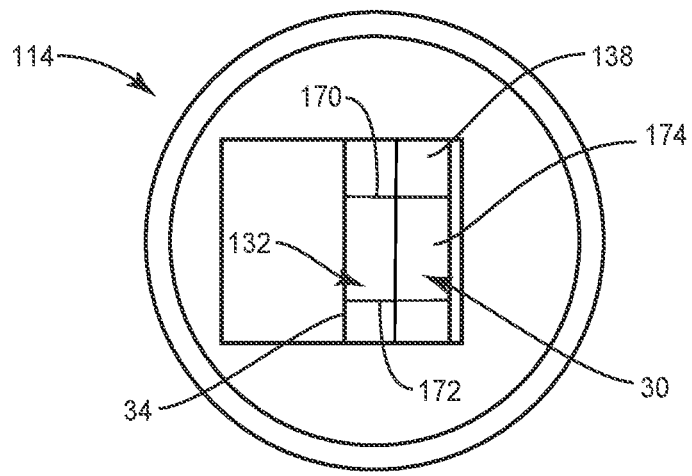

FIGS. 10-12 illustrate an alternative embodiment of a cap 114. Similar reference numbers will be used for features that are common to the cap 14 illustrated in FIGS. 3-5 and the cap 114 illustrated in FIGS. 10-12. In accordance with the alternative embodiment illustrated in FIGS. 10-12, the cap 114 includes at least one sealing member 132 with a plurality of slits 170, 172 designed to facilitate insertion of the test strip 50 through the access opening 30. Each sealing member 132 includes a first flexible tab 136 and a second flexible tab 138 opposite to the first flexible tab 136. The first and second flexible tabs 136, 138 extend inward into contact with each other to define the dynamic strip interface 34.

Continuing with FIGS. 10-12, each flexible tab 136, 138 includes at least a first slit 170 and a second slit 172 that each extend in a direction toward the dynamic strip interface 34. The first slit 170 and the second slit 172 defines a movable portion 174 therebetween that slides along reagent pads as the test strip 50 is moved through the access opening 30. As noted above, each reagent pad defines a width dimension 62 that is perpendicular to a length X of test strip 50. The moveable portion 174 defines a width 178 that extends from the first slit 170 to the second slit 172 that is no less than the width dimension 62 of each reagent pad.

Still referring to FIGS. 10-12, as the test strip 50 is inserted into the access opening 30 and through the dynamic strip interface 34, the moveable portion 174 flexes so as to slide along the reagent pad. When the test strip 50 is removed from the access opening 30, the moveable portion 174 reverts back to its original state. Provision of the slits and moveable portion 174 allows sample S adhered to the reagent pad to be scraped off of the reagent pad and back into the collection tube. Because the moveable portion 174 corresponds to the width dimension of the reagent pad, as the sealing member 132 flexes over the reagent pad, gaps between the sealing member and non-reactive surface 52 of the test strip 50 are minimized, which reduces the likelihood that sample S might escape from the collection tube 12 through the access opening 30. As illustrated, the first flexible tab 136 is longer than the second flexible tab 138 such that the dynamic strip interface 34 is proximate to a side of the access opening. It should be appreciated that the sealing member may include a single flexible tab that spans the access opening 30.

Figure 13:
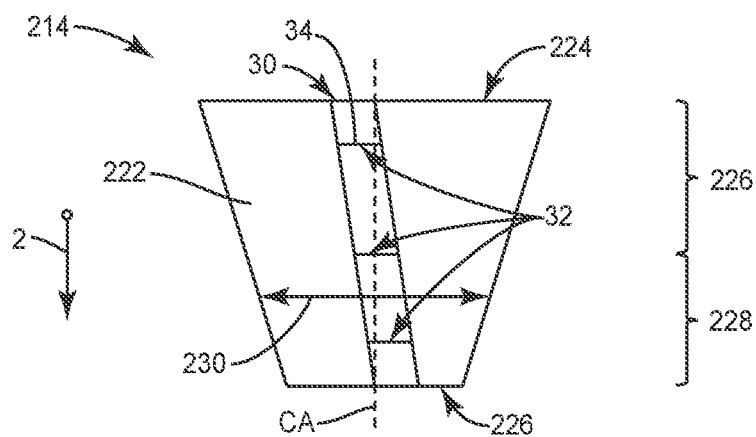
FIG. 13 is a side view of a cap according to another embodiment of the present disclosure.

FIG. 13 illustrates another alternative embodiment of a cap 214. In accordance with the alternative embodiment illustrated in FIG. 13, the cap 214 is sized for coupling to a plurality of different sized collection tubes 12 (collection tube not shown in FIG. 13). Similar reference numbers will be used for features that are common to the cap 14 illustrated in FIGS. 3-5 and the cap 214 illustrated in FIG. 13. In accordance with the illustrated embodiment, the cap 214 includes a cap body 222 having an upper end 224, a lower end 226 opposite the upper end 224, and an access opening 30 that extends through the cap body 222. The cap 214 also includes at least one sealing member 32 aligned with the access opening 30. Each sealing member 32 defines a dynamic strip interface 34. The cap 214 may include one sealing member or a plurality of sealing members 32. The cap body 222 has a proximal portion 227 and a distal coupling portion 228 spaced from the proximal portion 227 along a cap axis CA in a distal direction 2. The distal coupling portion 228 couples to the open end 20 (not shown) of the collection tube. As illustrated, the distal coupling portion 228 is tapered and defines an outer cross-sectional dimension 230 that decreases as it extends along the cap axis CA in the distal direction 2. The tapered shape permits the cap 214 to be coupled to collection tubes that have different cross-sectional dimension C. It can be said that cap 214 is a universal cap for coupling to different sized collection tubes.

Figure 14:
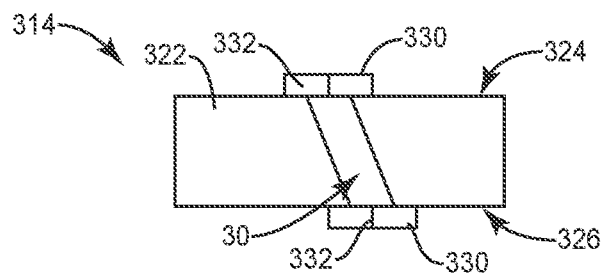
FIG. 14 is a side view of a cap according to another embodiment of the present disclosure.

FIG. 14 illustrates another alternative embodiment of a cap 314. Similar reference numbers will be used for features that are common to the cap 14 illustrated in FIGS. 3-5 and the cap 314 illustrated in FIG. 14. In accordance with the alternative embodiment illustrated in FIG. 14, the cap 314 is includes a cap body 322 with an upper end 324, a lower end 326, and an access opening 30 that extends from the upper end to the lower end 326. An inner surface 25 defines the access opening 30, which can be angled or parallel with respect to central longitudinal axis A of the collection tube 12 to which it is coupled to. The cap 14 includes a one or more panels 330 attached to the upper end 324 of the cap body 322. The panel 330 can be a planer shaped member or other piece of material that is attached to the upper end 324 of the cap body 322. The panel 330 may include a slit 332 that defines the dynamic strip interface 34. The panel 330 can be fixed to either or both of the upper end 324 and the lower end 326 of the cap such that slit 332 is aligned with the access opening 30. The test strip 50 can be used with the cap 314 and the collection tube 12 as described above with respect to the collection unit 10 illustrated in FIGS. 1-9.

Figure 15:
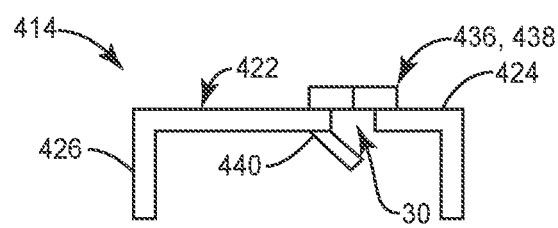
FIG. 15 is a side view of a cap according to another embodiment of the present disclosure.

FIG. 15 illustrates another alternative embodiment of a cap 414. Similar reference numbers will be used for features that are common to the cap 14 illustrated in FIGS. 3-5 and the cap 414 illustrated in FIG. 15. In accordance with the alternative embodiment illustrated in FIG. 15, the cap 414 includes a cap body 422 with an upper plate 424 that defines an access opening 30, and sidewalls 426 that extend from the upper plate 424 that are adapted to couple to the upper end 20 of the collection tube 12. The cap 414 may include a deflection member 440 proximate to the access opening 30. The deflection member 440 is angularly offset with respect to the access opening 30. The deflection member 440 is arranged next to the access opening 30 to force the test strip 50 toward and into contact with the sidewall 19 of the collection tube 12 so that the portion of the test strip 50 that contains the reagent pads 54 is substantially parallel to the sidewall 19 of collection tube 12 when in the inserted position (see FIGS. 6 and 9). As discussed above, deflection of the test strip 50 toward the sidewall 19 makes it easier to wet each reagent pad 54—especially when there is low sample volume. A pair of flexible tabs 436 and 438 can be coupled to the upper plate 424 to cover the access opening 30. The test strip 50 can be used with the cap 414 and the collection tube 12 as described above with respect to the collection unit 10 illustrated in FIGS. 1-9.

Figure 16:
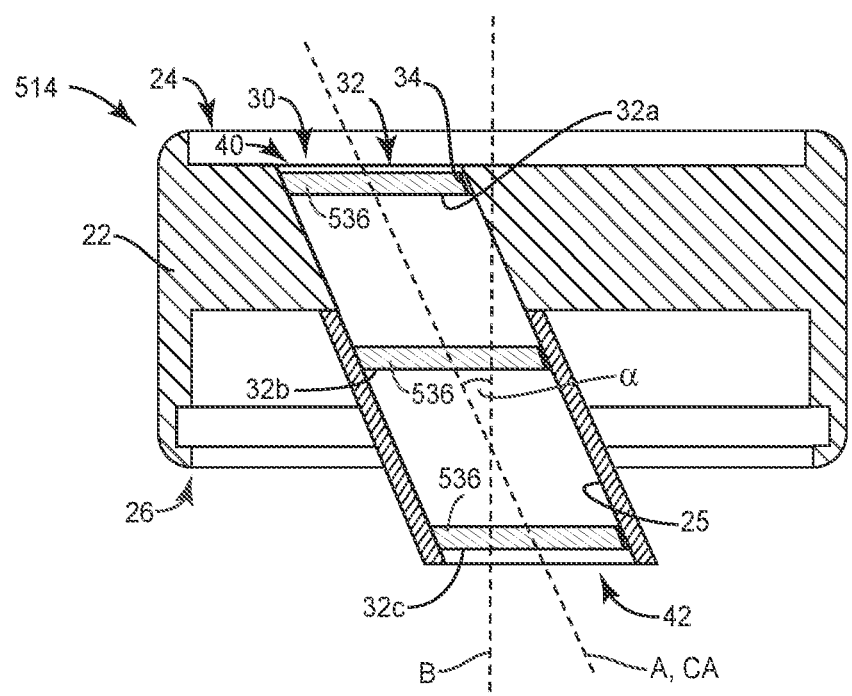
FIG. 16 is a cross-sectional side view of a cap according to embodiments of the present disclosure.

Those skilled in the art should recognize that while the embodiments described above illustrate a sealing member 32 with first and second flexible tabs 36 and 38, those same embodiments can also be implemented with a single flexible tab rather than two. In these alternative embodiments, a single flexible tab spans the access opening 30 such that a terminal end contacts the inner surface 25 of the cap body 22 so as to define the dynamic strip interface 34 when the flexible tab is in a closed position. As shown in FIG. 16, which is a variation of the embodiment shown in FIG. 5 and described above, is one such example. FIG. 16 uses similar reference numbers to identify features that are common to the cap 14 illustrated in FIG. 5 and the cap 514 illustrated in FIG. 16. In FIG. 16, each sealing member 32 in cap 514 has only one flexible tab 536—which abuts the inner surface 25 of the cap body 22, rather than abutting a flexible tab 38 as in FIG. 5, so as to define the dynamic strip interface 34 between the flexible tab 536 and the inner surface 25. When a test strip 50 is inserted it causes the single flexible tab 536 to bend so as to permit the test strip 50 to pass between the terminal end of flexible tab 536 and inner surface 25. When the test strip 50 is removed, the single flexible tab 536 retracts back into contact with the inner surface 25 of the cap body 22. It should be appreciated that the embodiments in FIGS. 10-15 can be similarly modified to include a single flexible tab.

The invention as described in the present disclosure is capable of exploitation in industry in accordance with how it can be made and/or used.

Those skilled in the art will also appreciate that the present disclosure may be applied to other applications and may be modified without departing from the scope of the present disclosure. Accordingly, the scope of the present disclosure is not intended to be limited to the exemplary embodiments described above, but only by the appended claims.

The following is a number list of non-limiting, illustrative embodiments of the inventive concept disclosed herein:

1. A sample collection unit configured to receive a test strip, the sample collection unit comprising:
    a collection tube including an open end; and
    a cap configured to be coupled to the open end to close the collection tube, the cap including an access opening that extends through the cap and at least one sealing member aligned with the access opening, the at least one sealing member including a dynamic strip interface that permits insertion of the test strip through the access opening and into the collection tube when the cap is coupled to the open end of the collection tube. \

2. The sample collection unit according to illustrative embodiment 1, wherein the cap inhibits a biological sample inside the collection tube from exiting the collection tube when a) the cap is coupled to the collection tube, and b) the test strip is inserted into the collection tube through the dynamic strip interface.

3. The sample collection unit according to illustrative embodiment 1, wherein the access opening includes a first end and a second end that opens into the collection tube, wherein the second end of the access opening is offset with respect to the first end to an extent that inhibits the sample inside the collection tube entering the second end of the access opening from exiting the first end of the access opening when the collection tube is turned on its side.

4. The sample collection unit of any one illustrative embodiments 1 to 3, wherein the collection tube is elongate along a longitudinal axis, and the access opening is elongate along an access opening axis that is angularly offset with respect to the longitudinal axis.

5. The sample collection unit of illustrative embodiment 4, wherein the access opening axis and the longitudinal axis define an acute angle.

6. The sample collection unit of any one illustrative embodiments 1 to 5, wherein each dynamic strip interface 1) permits insertion of the test strip into the collection tube, and 2) inhibits the sample inside the collection tube from exiting the collection tube when the test strip is inserted through the access opening.

7. The sample collection unit of any one illustrative embodiments 1 to 6, wherein each sealing member includes a first flexible tab and a second flexible tab opposite the first flexible tab and that extends into contact with the first flexible tab so as to define the dynamic strip interface.

8. The sample collection unit of illustrative embodiment 7, wherein the first flexible tab and the second flexible tab flex so as to slide along opposed surfaces of the test strip as the test strip is moved through the access opening.

9. The sample collection unit of illustrative embodiment 7 or illustrative embodiment 8, wherein the test strip has at least one test area, wherein one of the first and second flexible tabs include at least a first slit and a second slit that each extend in a direction toward the dynamic strip interface, the first and second slits defining a movable portion that slides along the at least one test area as the test strip is moved through the access opening.

10. The sample collection unit of illustrative embodiment 9, wherein each test area is defined by a reagent pad, wherein each reagent pad defines a width dimension that is perpendicular to a length of the test strip, wherein the moveable portion defines a width that extends from the first slit to the second slit that is no less than the width dimension of each reagent pad.

11. The sample collection unit of any one illustrative embodiments 1 to 10, wherein the at least one sealing member is a plurality of sealing members that are spaced apart with respect to each other along the access opening.

12. The sample collection unit of illustrative embodiment 11, wherein the test strip has at least one test area, wherein each test area is defined by a reagent pad, wherein each reagent pad has a length dimension that is aligned with a length of the test strip, wherein adjacent sealing members of the plurality of sealing members are spaced apart with respect to each other at a distance that is no less than the length dimension of each respective reagent pad of the test strip.

13. The sample collection unit of any one illustrative embodiments 1 to 13, wherein the cap is sized for coupling to a plurality of different sized collection tubes.

14. The sample collection unit of illustrative embodiment 13, wherein the cap includes a cap body having a proximal portion and a distal coupling portion spaced from the proximal portion along a cap axis in a distal direction, wherein the distal coupling portion couples to the open end of the collection tube, the distal coupling portion further defining an outer cross-sectional dimension that decreases as it extends along the cap axis in the distal direction.

15. A biological sample analysis kit, comprising:
a test strip that includes at least one test area;
a collection tube including an open end; and
a cap including an access opening that extends through the cap and at least one sealing member aligned with the access opening, the at least one sealing member including a dynamic strip interface that permits the test strip to be inserted into through the access opening and into the collection tube when the cap is coupled to the open end of the collection tube.

16. The biological sample analysis kit of illustrative embodiment 15, wherein the cap inhibits a biological sample inside the collection tube from exiting the collection tube when a) the cap is coupled to the collection tube, and b) the test strip is inserted into the collection tube through the dynamic strip interface.

17. The biological sample analysis kit of illustrative embodiment 16 or illustrative embodiment 16, wherein the access opening includes a first end and a second end that opens into the collection tube, wherein the second end of the access opening is offset with respect to the first end to an extent that inhibits the sample inside the collection tube entering the second end of the access opening from exiting the first end of the access opening when the collection tube is turned on its side.

18. The biological sample analysis kit of any one illustrative embodiments 15 to 17, wherein the collection tube is elongate along a longitudinal axis, and the access opening is elongate along an access opening axis that is angularly offset with respect to the longitudinal axis.

19. The biological sample analysis kit of illustrative embodiment 19, wherein the access opening axis and the longitudinal axis define an acute angle.

20. The biological sample analysis kit of any one illustrative embodiments 15 to 19, wherein each dynamic strip interface 1) permits insertion of the test strip into the collection tube, and 2) inhibits the sample inside the collection tube from exiting the collection tube when the test strip is inserted through the access opening and the collection tube is turned on its side.

21. The biological sample analysis kit unit of any one illustrative embodiments 15 to 20, wherein each sealing member includes a first flexible tab and a second flexible tab opposite to the first flexible tab and that extends into contact with the first flexible tab so as to define the dynamic strip interface for insertion of the test strip.

22. The biological sample analysis kit of illustrative embodiment 21, wherein the first flexible tab and the second flexible tab flex so as to slide along opposed surfaces of the test strip as the test strip is moved through the access opening.

23. The biological sample analysis kit illustrative embodiment 21 or illustrative embodiment 22, wherein the test strip has at least one test area, wherein one of the first and second flexible tabs include at least a first slit and a second slit that each extend in a direction toward the dynamic strip interface, the first and second slits defining a movable portion that slides along the at least one test area as the test strip is moved through the access opening.

24. The biological sample analysis kit of illustrative embodiment 23, wherein each test area is defined by a reagent pad, wherein each reagent pad defines a width dimension that is perpendicular to a length of test strip, wherein the moveable portion defines a width that extends from the first slit to the second slit that is no less than the width dimension of each reagent pad.

25. The biological sample analysis kit of any one illustrative embodiments 15 to 24, wherein the at least one sealing member is a plurality of sealing members that are spaced apart with respect to each other along the access opening.

26. The biological sample analysis kit of illustrative embodiment 26, wherein the test strip has at least one test area, wherein each test area is defined by a reagent pad, and each reagent pad has a length dimension that is aligned with a length of the test strip, wherein adjacent sealing members of the plurality of sealing members are spaced apart with respect to each other at a distance that is no less than the length dimension of each respective reagent pad of the test strip.

27. The biological sample analysis kit of any one illustrative embodiments 15 to 26, wherein the cap is sized for coupling to a plurality of different sized collection tubes.

28. The biological sample analysis kit of illustrative embodiment 29, wherein the cap includes a cap body having a proximal portion and a distal coupling portion spaced from the proximal portion along a cap axis in a distal direction, wherein the distal coupling portion couples to the open end of the collection tube, the distal coupling portion further defining an outer cross-sectional dimension that decreases as it extends along the cap axis in the distal direction.

29. A cap for coupling to an open end of a sample collection tube, the cap comprising:
a cap body having an upper end, a lower end opposite the upper end, an access opening that extends through the cap body, and at least one sealing member aligned with the access opening, the at least one sealing member including a dynamic strip interface, wherein the dynamic strip interface permits insertion of a test strip through the access opening.

30. The cap of illustrative embodiment 29, wherein the cap inhibits the sample inside the collection tube from exiting the collection tube through the access opening when a) the cap is coupled to the collection tube, b) the test strip is inserted through the dynamic strip interface.

31. The cap of illustrative embodiment 29 or illustrative embodiment 30, wherein the access opening includes a first end and a second end that opens into the collection tube, wherein the second end of the access opening is offset with respect to the first end to an extent that inhibits the sample inside the collection tube entering the second end of the access opening from exiting the first end of the access opening when the collection tube is turned on its side.

32. The cap of any one illustrative embodiments 29 to 31, wherein the cap defines a cap central axis, and the access opening is elongate along an access opening axis that is angularly offset with respect to the cap central axis.

33. The cap of illustrative embodiment 32, wherein the access opening axis and the longitudinal axis define an acute angle.

34. The cap of any one illustrative embodiments 29 to 33, wherein each sealing member includes a first flexible tab and a second flexible tab opposite to the first flexible tab and that extends into contact with the first flexible tab so as to define the dynamic strip interface.

35. The cap of illustrative embodiment 33 or illustrative embodiment 35, wherein the test strip has a plurality of pads, wherein one of the first and second flexible tabs include at least a first slit and a second slit that each extend in a direction toward the dynamic strip interface, the first and second slits defining a movable portion that slides along the plurality of the pads as the test strip is moved through the access opening.

36. The cap of any one illustrative embodiments 29 to 35, wherein the at least one sealing member is a plurality of sealing members that are spaced apart with respect to each other along the access opening.

37. The cap of illustrative embodiment 29, wherein the cap includes a cap body having a proximal portion and a distal coupling portion spaced from the proximal portion along a cap axis in a distal direction, wherein the distal coupling portion couples to the open end of the collection tube, the distal coupling portion further defining an outer cross-sectional dimension that decreases as it extends along the cap axis in the distal direction.

The invention claimed is:

1. A sample collection unit configured to receive a test strip, the sample collection unit comprising:
    a collection tube including an open end and being elongate along a longitudinal axis; and
    a cap configured to be coupled to the open end to close the collection tube, the cap including an access opening that extends through the cap and at least one sealing member aligned with the access opening, the at least one sealing member including a dynamic strip interface that permits insertion of the test strip through the access opening and into the collection tube when the cap is coupled to the open end of the collection tube, the access opening being elongate along an access opening axis that is angularly offset with respect to the longitudinal axis.

2. The sample collection unit of claim 1, wherein the cap inhibits a biological sample inside the collection tube from exiting the collection tube both when a) the cap is coupled to the collection tube, and when b) the test strip is inserted into the collection tube through the dynamic strip interface.

3. The sample collection unit of claim 1, wherein the access opening includes a first end and a second end that opens into the collection tube, wherein the second end of the access opening is offset with respect to the first end to an extent that inhibits the sample inside the collection tube entering the second end of the access opening from exiting the first end of the access opening when the collection tube is turned on its side.

4. The sample collection unit of claim 1, wherein the access opening axis and the longitudinal axis define an acute angle.

5. The sample collection unit of claim 1, wherein each sealing member includes a first flexible tab and a second flexible tab opposite the first flexible tab and that extends into contact with the first flexible tab so as to define the dynamic strip interface.

6. The sample collection unit of claim 5, wherein the first flexible tab and the second flexible tab flex so as to slide along opposed surfaces of the test strip as the test strip is moved through the access opening.

7. The sample collection unit of claim 5, wherein one of the first and second flexible tabs include at least a first slit and a second slit that each extend in a direction toward the dynamic strip interface, the first and second slits defining a movable portion that slides along at least one test area of the test strip as the test strip is moved through the access opening.

8. The sample collection unit of claim 1, wherein the at least one sealing member is a plurality of sealing members that are spaced apart with respect to each other along the access opening.

9. The sample collection unit of claim 1, wherein the cap is sized for coupling to a plurality of different sized collection tubes.

10. The sample collection unit of claim 9, wherein the cap includes a cap body having a proximal portion and a distal coupling portion spaced from the proximal portion along a cap axis in a distal direction, wherein the distal coupling portion couples to the open end of the collection tube, the distal coupling portion further defining an outer cross-sectional dimension that decreases as it extends along the cap axis in the distal direction.

11. A biological sample analysis kit, comprising:
    the sample collection unit according to claim 1, and the test strip that includes at least one test area.

12. The biological sample analysis kit unit of claim 11, wherein each sealing member includes a first flexible tab and a second flexible tab opposite to the first flexible tab and that extends into contact with the first flexible tab so as to define the dynamic strip interface for insertion of the test strip.

13. The biological sample analysis kit of claim 12, wherein one of the first and second flexible tabs include at least a first slit and a second slit that each extend in a direction toward the dynamic strip interface, the first and second slits defining a movable portion that slides along the at least one test area as the test strip is moved through the access opening.

14. The biological sample analysis kit of claim 13, wherein each test area is defined by a reagent pad, wherein each reagent pad defines a width dimension that is perpendicular to a length of test strip, wherein the moveable portion defines a width that extends from the first slit to the second slit that is no less than the width dimension of each reagent pad.

15. The biological sample analysis kit of claim 11, wherein the at least one sealing member is a plurality of sealing members that are spaced apart with respect to each other along the access opening.

16. The biological sample analysis kit of claim 15, wherein each test area is defined by a reagent pad, and each reagent pad has a length dimension that is aligned with a length of the test strip, wherein adjacent sealing members of the plurality of sealing members are spaced apart with respect to each other at a distance that is no less than the length dimension of each respective reagent pad of the test strip.

17. A method, comprising:
inserting the test strip including at least one test area into the access opening of the cap coupled to the open end of the collection tube, the cap and the collection tube being components of the sample collection unit according to claim 1; and
advancing the test strip such that the test strip engages a sidewall of the collection tube and guides the test strip along the sidewall of the collection tube until the test area is submerged in a biological sample within the collection tube.

* * * * *